United States Patent [19]

Tsumura et al.

[11] 4,001,082
[45] Jan. 4, 1977

[54] METHOD OF ISOMERIZING GLUCOSE WITH ENZYME IMMOBILIZED WITHIN MICROBIAL CELL

[75] Inventors: Nobuzo Tsumura; Takafumi Kasumi, both of Tokyo, Japan

[73] Assignee: Director of National Food Research Institute, Tokyo, Japan

[22] Filed: Feb. 26, 1976

[21] Appl. No.: 661,730

[30] Foreign Application Priority Data

Oct. 2, 1975  Japan ..................... 50-118262

[52] U.S. Cl. ................. 195/31 F; 195/63; 195/65; 195/68; 195/DIG. 11

[51] Int. Cl.[2] ............................ C12D 13/02

[58] Field of Search .......... 195/65, 63, 68, 31 F, 195/DIG. 11, 116, 52, 56, 59, 104

[56] References Cited

UNITED STATES PATENTS

| | | | |
|---|---|---|---|
| 3,553,310 | 1/1971 | Csizmas et al. | 195/68 X |
| 3,623,953 | 11/1971 | Cotter et al. | 195/31 F |
| 3,715,276 | 2/1973 | Takasaki et al. | 195/31 F |
| 3,821,082 | 6/1974 | Lamm et al. | 195/31 F |
| 3,821,086 | 6/1974 | Lee et al. | 195/65 X |
| 3,933,587 | 1/1976 | Maeda et al. | 195/68 |
| 3,957,580 | 5/1976 | Nelson | 195/31 F |

OTHER PUBLICATIONS

Shashkova et al., "Interaction of lysozyme with Low-Molecular-Weight Inhibitors and Modified Substrates Containing B-(1-4) and (1970) B-(1-6)--glucosamine bonds, *Chemical Abstracts*, vol. 72, No. 21, Abs. No. 107325, p. 35.

Tusmura et al., "Enzymic Conversion of D-Glucose to D-Fructose, Part IV, Cultivation Methods for *Aerobacter Cloacae*," *Shokuryo Kenkyusho Kenkyu Hokoku*, No. 19, pp. 189–193, (1965).

*Primary Examiner*—A. Louis Monacell
*Assistant Examiner*—Thomas G. Wiseman
*Attorney, Agent, or Firm*—Flynn & Frishauf

[57] ABSTRACT

A method of isomerizing glucose with an enzyme immobilized within a microbial cell has been developed. The immobilized enzyme is prepared by dipping a microbial cell containing glucose isomerase in an aqueous solution containing citric acid and drying it, if necessary. An immobilization of an intracellular enzyme is reinforced by supplemental means such as radiation or others.

22 Claims, No Drawings

METHOD OF ISOMERIZING GLUCOSE WITH ENZYME IMMOBILIZED WITHIN MICROBIAL CELL

BACKGROUND OF THE INVENTION

1. Field of the Invention

The present invention relates to a method of isomerizing glucose with a microbial cell having glucose isomerase immobilized therein.

As already known, glucose isomerase is produced by certain kinds of bacteria, such as Actinomycetes, and accumulated within their cells. Therefore, it is possible to use cells obtained by cultivation as a crude enzyme source for isomerizing glucose. In usual microbial cells, however, the amount of enzyme which flows out of cells during a batch reaction and impossible to be recovered is substantial, though a part of the enzyme remains in the cells, and it can be recovered and reused. Generally, the liberation of the enzyme from microbial cells becomes extremely large when the cells are used after drying. Subsequently, it is clear that if enzyme liberation from microbial cells were prevented by an immobilization technique and these cells obtained in a dry state, economy and efficiency in enzyme utilization, including transportation, storage and use, would be improved substantially.

2. Description of the Prior Art

By immobilizing an enzyme, its long-term use or repeated use by recovery is made possible and advantages such as reduction of reaction time, continuation and automatization of reaction, etc., are realized. Therefore, various methods for immobilization have been tried with different kinds of enzymes. With regard to glucose isomerase, various methods for immobilization have been reported for cell-free enzymes as well as intracellular enzymes.

Adsorption, entrapment and covalent bonding methods and others have been tried with free glucose isomerase. However, as glucose isomerase is an intracellular enzyme as above-mentioned, it is more convenient if this enzyme can be immobilized within a microbial cell and retained for a long time. Whole cell immobilization does not necessitate a process such as extraction or purification of the enzyme to obtain a cell-free enzyme, and is also free from enzyme inactivation or enzyme leakage at the time of combining the enzyme with a carrier.

As the methods for immobilizing intracellular glucose isomerase, the method of heat-treating microbial cells (Y. Takasaki and A. Kambayashi; Rep. Ferment. Res. Inst. (Japan), 37, 31–37 (1969)), treating microbial cells with a sulfite (N.E. Lloyd, L.T. Lewis, R.M. Logan and D.N. Patel; U.S. Pat. No. 3,694,314, Sept. 26, 1972), incorporating microbial cells into a water-insoluble polymer (Jun Owaki, Yoshiro Minami; Japanese Laid Open Patent Gazette; No. 29,786/1975, Mar. 25, 1975; W.R. Vieth, S.S. Wang and R. Saini; Biotech. Bioeng. 15, 565 (1973)), flocculating microbial cells with a polyelectrolyte (C.K. Lee and M.E. Long; U.S. Pat. No. 3,821,086; June 28, 1974), and treating microbial cells with various metal salts (W.R. Lamm, L.G. Davis and R.G. Dworschak; U.S. Pat. No. 3,821,082; June 28, 1974), etc., are known to date.

The method of the present invention is an extremely simple and effective one, in which intracellular glucose isomerase is immobilized by specific means completely different from conventional methods.

SUMMARY OF THE INVENTION

The present invention relates to a method of isomerizing glucose into fructose with microbial cells containing an enzyme. More specifically, this invention provides a method of isomerizing glucose with an enzyme immobilized within microbial cells which is prepared by treating microbial cells containing glucose isomerase with an aqueous solution containing citric acid and/or a citrate of a specified metal.

DETAILED EXPLANATION OF THE INVENTION

The present invention provides a simple and effective method of treating microbial cells containing glucose isomerase and utilizing these cells in either a batch- or continuous-type process for isomerization. As the microorganisms containing glucose isomerase, those belonging to genus of Aerobacter, Lactobacillus, Brevibacterium, Bacillus, Arthrobacter, Streptomyces, Nocardia, Micromonospora, Microbispora, Microellobospora, Streptosporangium, Leuconostoc, Pasteurella and Actinoplanes are known. Any of these microorganisms can be applied to the method of the present invention. Microorganisms are known to be denaturated or aggregated by various protein denaturants such as an aldehyde, acid, salt of heavy metal, organic solvent, etc. Some of them denaturate and inactivate an enzyme and are harmful from a hygienic viewpoint, and these are not appropriate for the purpose of the present invention.

We have tried to treat microbial cells with various kinds of organic and inorganic acids under proper pH conditions. For instance, hydrochloric and sulfuric acids as inorganic acids, and oxalic, lactic, succinic, maleic, tartaric, aspartic, tannic, citric acids and gum arabic, etc., as organic acids have been tested as treating reagents. As a result, it has been found that citric acid is particularly advantageous. That is, we have discovered that enzyme retentivity of microbial cells at reaction time is significantly improved by dipping the said cells in a solution containing citric acid and/or a citrate of a specified metal (defined as "citrate solution" hereafter) and then, if required, drying these microbial cells.

As metals of a citric acid salt, monovalent and divalent cations and a mixture thereof (for instance, lithium, sodium and potassium as monovalent metals, and magnesium, cobalt and calcium as divalent metals) are used. Thus, the method of glucose isomerization using an intracellular enzyme wherein the enzyme is effectively immobilized with little loss has been realized.

The method of treating microbial cells containing glucose isomerase comprises dipping said cells in a citrate solution at a pH range wherein no significant damage to the enzyme occurs, and then, if required, drying said cells at a temperature at which the enzyme is not significantly inactivated.

The method of the present invention is applied to both intact and heat treated cells of bacteria such as Actinomycetes. In the case of intact cells, the method of the present invention is applied to the cells separated from a cultivation broth. As the effect of treatment is more significant with heat-treated cells than with intact cells, it is preferred to use heat-treated cells. The heating is done at a temperature killing intact cells, and usually a temperature of from 60° to 85° C. is preferred.

With regard to concentration of citric acid and/or a citrate in a citrate solution, the effect is observed at 0.1% or more calculated as citric acid, but a concentration of from 2 to 8% as citric acid gives favorable results. The volume of this solution is preferred to be one in which microbial cells are dispersed readily with agitation and, specifically, 40 – 150 times by weight of dried cells therein. The effect of citrate treatment on improvement of enzyme retentivity of microbial cells varies somewhat depending on the kind or the state of said cells. For example, it has been observed that a heat treatment of the cells, the retention period after harvesting of the cell and also a pretreatment of the cell with a flocculating agent, etc., influence somewhat on the effect of citrate treatment.

The frequency of dipping microbial cells in a citrate solution is arbitrary. It is effective to repeat dipping and separation more than twice when a citrate solution of low concentration is used.

A citrate solution is used at a broad pH range without significant loss of glucose isomerase activity, though at pH below 5 the enzyme is apt to be inactivated. However, the tendency that the enzyme-retaining effect of treated microbial cells is lowered as pH rises from acidic to alkaline is recognized, and so it is preferred to adjust pH to from 5 to 8, more preferably to 5–6.

The effect of citrate treatment on the cells at a broad range of temperature is recognized. The cells are dipped in a citrate solution at a temperature not inactivating glucose isomerase significantly, i.e., from 0° to 80° C., preferably 0° – 40° C., and retained for a sufficient time for full immersion of the cells in the solution, and then recovered by centrifuge or filtration. In addition to this, drying of the cells after dipping treatment reinforces the effect of the citrate treatment. As drying methods, air-drying at room temperature, drying under reduced pressure, heat-drying, dehydration and drying with organic solvents, lyophilization, etc., can be effectively applied. In the case of heat-drying, it is possible to dry at any temperature which does not cause significant inactivation of the enzyme, but preferably a temperature below 50° C. is used.

The method of the present invention can be applied not only to intact cells or heat-treated cells, but also effectively to cells aggregated in advance by a pretreatment with a flocculant. For instance, microbial cells such as Streptomyces aggregated with an acidic solution of chitosan obtained from chitin by deacetylation can be improved substantially in glucose isomerase retentivity by dipping in a citrate solution and then drying. Reverse order of the treatment with a citrate solution and a flocculant also can be used effectively. The flocculant referred to here is one which generally aggregates microbial cells; these include negative and positive polyelectrolytes, inorganic hydrated colloids etc.

Furthermore, the effect of a citrate treatment of microbial cells can be improved by various supplemental means. For instance, enzyme retentivity of the cell treated with a citrate solution is reinforced by additional treatment with ionizing radiation such as γ-rays. It is also effective to treat microbial cells with a reagent effecting protein denaturation including sodium sulfite, cysteine, urea and glutaraldehyde at the same time, or approximating that time, as the treatment with citric acid.

As a result of the aforesaid treatment, glucose isomerase is immobilized within microbial cells containing it and is difficult to liberate. Therefore, in a batchwise isomerization reaction, these treated microbial cells can be used repeatedly by recovering them. In addition, the reaction time can be reduced by using the cells in large quantities under premising their recovery. In addition, automatization of the process and labor saving can be attained in a continuous-type isomerization reaction by packing the treated microbial cell in a column. In either continuous- or batch-type process, the reduction of reaction time is significantly effective to prevent coloring of reaction solution and induces drastic curtailment of the expenses for purification of a sugar solution. According to the present invention, isomerization of glucose can be done with remarkable benefits.

The present invention is further illustrated in the following Examples, which are not to be considered to limit the invention.

EXAMPLE 1

Two grams of commercial frozen cells of Actinomycetes containing glucose isomerase (belonging to genus Streptomyces, heat-treated, with ca. 60% moisture; "Godo-AGI" produced by Godo Shusei K.K.) were dipped in 50 ml. of 0 – 16% citrate solution (adjusted to pH 6.0 with sodium hydroxide), stored at 4° C overnight and then centrifuged. The sludge of the microbial cells was air-dried on a Petri dish for 5 days.

40 mg. of dried cells (as solid) thus obtained were dispersed in 6 ml. of reaction solution, sealed in 10 ml.-volume test tube and shaked for 20 hours at 60° C. for isomerization. The reaction solution is composed of glucose 40% (w/v), magnesium ion 0.02 M and phosphate buffer solution 0.025 M (pH 7.5).

After reaction, microbial cells were recovered by centrifugation and repeatedly used for 2nd and 3rd reactions with the addition of 6 ml. of fresh reaction solution. The amount of fructose produced in each reaction mixture was determined, and the remaining enzyme activity of microbial cells (enzyme retentivity) was expressed as the percentage of the amount of fructose produced in 2nd and 3rd reactions related to that of the 1st reaction. The amount of fructose produced by each sample was compared with one another in the initial reaction, and it served as relative activity. The results of these determinations are shown in Table 1.

Table 1

| Sample No. | 1 | 2 | 3 | 4 | 5 | 6 | 7 |
|---|---|---|---|---|---|---|---|
| Conc. of Citrate (%) | 0 | 0.1 | 1 | 4 | 8 | 12 | 16 |
| Cell Moisture (%) | 13.8 | 12.0 | 11.0 | 11.4 | 13.9 | 14.9 | 15.5 |
| Relative Activity (%) | 100 | 97 | 95 | 98 | 96 | 95 | 95 |
| Remaining Activity A (%) | 41 | 52 | 63 | 77 | 81 | 73 | 74 |
| Remaining Activity B (%) | 11 | 37 | 53 | 68 | 71 | 64 | 62 |

A: Remaining activity in 2nd reaction
B: Remaining activity in 3rd reaction.

EXAMPLE 2

Dry cells were obtained according to the procedure of Example 1, except that: the concentration of citric acid was 8%, the pH of the citrate solution varied from 5 to 9, and the dipping period was 1.5 hours.

The results of determinations made in the same way as Example 1 are shown in Table 2.

Table 2

| pH | 5.0 | 5.5 | 6.0 | 6.5 | 7.0 | 8.0 | 9.0 |
| --- | --- | --- | --- | --- | --- | --- | --- |
| Relative Activity (%) | 90 | 97 | 100 | 97 | 97 | 97 | 97 |
| Remaining Activity A (%)* | 81 | 77 | 79 | 71 | 67 | 67 | 63 |
| Remaining Activity B (%)* | 74 | 71 | 71 | 63 | 57 | 60 | 58 |

*Same as in Table 1, and also in the following Tables.

EXAMPLE 3

*Lactobacillus brevis* ATCC 8287 was cultivated by a known method (Agr. Biol Chem., 27, 271 (1963)) and microbial cells containing glucose isomerase were obtained. These intact cells of 350 mg. (as dry base) were dipped in 50 ml. of 8% citrate solution (pH 6.0) overnight and centrifuged. Then the sludge of microbial cells was air-dried on a Petri dish for 5 days.

Enzyme retentivity of the thus obtained dry cells was determined in the same way as in Example 1, except that the reaction solution used was 40% (w/v) glucose solution of pH 7.0 containing $10^{-3}$ M manganese ion, $10^{-4}$ M cobalt ion and $2 \times 10^{-2}$ M Tris-HCl buffer solution, and the reaction temperature was 50° C.

As a result, enzyme retentivity of the cells treated with citrate solution in the 2nd reaction was 58%, while that of the control cells was 20% in the 2nd reaction.

EXAMPLE 4

The intact cells obtained in Example 3 were heated at 55° C. for 10 minutes. Then dry cells treated with a citrate solution were obtained in the same way as in Example 3. The results of determinations in the same manner as in Example 3 showed that enzyme retentivity of cells treated with a citrate solution was 94% in the 2nd reaction and 88% in the 3rd reaction, while the value of a control sample dried after heat-treatment was 18% in the 2nd reaction and 5% in the 3rd reaction.

EXAMPLE 5

Two grams of commercial frozen cells belonging to genus Streptomyces (same as in Example 1) were dispersed in 50 ml. of 8% citrate solution (pH 6.0) and stored at 4° C. and 30° C. overnight. Then the cells were separated by centrifugation. These cells were used without drying and the percentage of remaining activity in the isomerization reaction was determined in the same way as in Example 1. The results are shown in Table 3.

Table 3

| Cells | Not Treated | Treated at 4° C. | Treated at 30° C. |
| --- | --- | --- | --- |
| Remaining Activity A (%) | 30 | 62 | 64 |
| Remaining Activity B (%) | 10 | 36 | 35 |

EXAMPLE 6

Each 5 g. of frozen cells of Streptomyces (same as in Example 1) were dispersed in 100 ml. of a 0.5% or a 1% citrate solution (pH 6.0) and left at room temperature for 2 hours. Then the cells were separated by centrifugation and air-dried overnight at 30° C. This treatment of dipping and drying was repeated up to 4 times and a sample was obtained each time. The percentage of remaining activity of intracellular enzyme was determined for these samples in the same way as in Example 1. The results are shown in Table 4.

As a control, non-treated dry microbial cells were used.

Table 4

| Treating times | 1 | 2 | 3 | 4 | not treated |
| --- | --- | --- | --- | --- | --- |
| Treated with 0.5% citrate: | | | | | |
| Relative Activity (%) | 96 | 76 | 75 | 59 | 100 |
| Remaining Activity A (%) | 74 | 70 | 83 | 82 | 37 |
| Remaining Activity B (%) | 47 | 54 | N.D.* | 72 | 20 |
| Treated with 1% citrate: | | | | | |
| Relative Activity (%) | 97 | 93 | 84 | 62 | 100 |
| Remaining Activity A (%) | 79 | 85 | 86 | 83 | 37 |
| Remaining Activity B (%) | 59 | 71 | 75 | 71 | 20 |

*N.D.: Not Determined

EXAMPLE 7

Ten grams of frozen cells of Streptomyces (same as those used in Example 1) were dispersed in 200 ml. of water, then 100 ml. of 0.2% chitosan solution (prepared by dissolving chitosan in a 0.5% acetic acid solution and adjusting pH to 6.0 with sodium hydroxide) was added to the suspension as a flocculant.

To aggregated cells obtained by filtration, 50 ml. of the aforesaid chitosan solution was again added and left for 1 hour. Then the cells were dehydrated by compression and each amount corresponding to 1/5 of the total amount was either (1) air-dried as it was, (2) dipped in 50 ml. of a 4% citrate solution (pH 6.0) overnight, filtered and air-dried, or (3) dipped in 50 ml. of a 12% citrate solution (pH 6.0) overnight, filtered and air-dried.

The moisture of these dry samples was approximately 13%, and enzyme activity per dry weight unit was not inferior to that of frozen cells of raw material. The result of the determination of enzyme retentivity of each sample is shown in Table 5. The determination method is the same as in Example 1.

Table 5

| Sample No. | (1) | (2) | (3) |
| --- | --- | --- | --- |
| Remaining Activity A (%) | 23 | 77 | 80 |
| Remaining Activity B (%) | 7 | 67 | 73 |

EXAMPLE 8

Microbial cells aggregated with chitosan in the same way as in Example 7 were treated with a citrate solution and a dry sample was obtained. In this case, the concentration of citric acid was 10%. The continuous reaction was carried out at 60° C. for a week by packing said dry sample (1.5 g.) in a column of 1 cm. diameter and 10 cm. length and passing 40% (w/v) glucose solution (containing $10^{-2}$ M magnesium and adjusted to pH 8 with alkali) at a velocity of SV = 0.6. The effluent solution was collected at intervals of 24 hours and the amount of fructose formed was determined. Fructose content in each sample is shown in Table 6 as the relative value to that in the 1st day's sample.

Table 6

| Reaction times (day) | 1 | 3 | 5 | 7 |
|---|---|---|---|---|
| Amount of Fructose produced | 100 | 101 | 98 | 98 |

EXAMPLE 9

Microbial cells of Streptomyces were dipped in a 8% citrate solution adjusted to pH 6.0 overnight in the same way as in Example 1 and centrifuged. The sludge of microbial cells was radiated by γ-rays at room temperature, then air-dried.

The change of enzyme retentivity of the irradiated dry sample is shown in Table 7. The determination method is the same as in Example 1. Enzyme activity was recognized not to be lowered by irradiation with γ-rays.

Table 7

| Dose (Krad) | 0 | 50 | 100 | 150 |
|---|---|---|---|---|
| Remaining Activity A (%) | 69 | 72 | 81 | 89 |
| Remaining Activity B (%) | 67 | 72 | 76 | 89 |

EXAMPLE 10

Two grams of frozen cells of Streptomyces (same as those in Example 1) were dispersed in 50 ml. of a 8% citrate solution (pH 6.0) either containing sodium sulfite or cysteine and retained for 2 hours at room temperature (about 20° C.). Then the microbial cells were separated and air-dried for 2 days at 30° C. The remaining activity of each sample repeatedly used for isomerization in the same way as in Example 1 is shown in Table 8.

Table 8

| Sample No.* | 1 | 2 | 3 | 4 | 5 | 6 |
|---|---|---|---|---|---|---|
| Remaining Activity A (%) | 67 | 77 | 79 | 75 | 79 | 76 |
| Remaining Activity B (%) | 53 | 66 | 70 | 55 | 65 | 65 |

*No. 1: 8% citrate solution
*No. 2: 8% citrate solution + $10^{-4}$ M $Na_2SO_3$
*No. 3: 8% citrate solution + $10^{-3}$ M $Na_2SO_3$
*No. 4: 8% citrate solution + $10^{-2}$ M $Na_2SO_3$
*No. 5: 8% citrate solution + $10^{-4}$ M Cysteine
*No. 6: 8% citrate solution + $10^{-3}$ M Cysteine

EXAMPLE 11

Two grams of frozen cells of Streptomyces (same as those used in Example 1) were dipped in 50 ml. of 4% citrate solution (pH 6) and left overnight. Then the microbial cells were separated and air-dried; they are identified as Sample-II. As a control, air-dried cells from original frozen cells were identified as Sample-I. Each 40 mg. (as dry base) of Sample-I and Sample-II were weighed and 5 ml. of 1% glutaraldehyde in 0.04 M phosphate buffer, pH 7.0, was added to each. Each resulting mixture was agitated and then the microbial cells were washed with water twice by centrifuge within 30 minutes. They were identified as Sample-III (obtained from Sample-I) and Sample-IV (obtained from Sample-II). These samples were used for isomerization and enzyme retentivity was determined. The results are shown in Table 9.

Table 9

| Sample No. | I | II | III | IV |
|---|---|---|---|---|
| Relative Activity (%) | 100 | 100 | 86 | 69 |
| Remaining Activity A (%) | 33 | 82 | 48 | 89 |
| Remaining Activity B (%) | 19 | 70 | 33 | 86 |

What is claimed is:

1. A method of isomerizing glucose to fructose which comprises contacting an aqueous solution of glucose under conditions suitable for isomerization with a microbial cell having glucose isomerase immobilized therein, said microbial cell being prepared by dipping a microorganism containing glucose isomerase in an aqueous solution of citric acid or of a metal salt thereof, said metal being selected from the group of lithium, sodium, potassium, magnesium, cobalt, calcium and mixtures thereof.

2. Process according to claim 1, wherein said microbial cell is dried after said dipping and prior to said contact.

3. Process according to claim 1, wherein said microbial cell is an intact cell.

4. Process according to claim 1, wherein said microbial cell is a heat-treated cell.

5. Process according to claim 1, wherein the microbial cell is a bacteria.

6. Process according to claim 1, wherein the microbial cell is selected from the group consisting of Aerobacter, Lactobacillus, Brevibacterium, Bacillus, Arthrobacter, Streptomyces, Nocardia, Micromonospora, Microbispora, Microellobospora, Streptosporangium, Leuconostoc, Pasteurella and Actinoplanes.

7. Process according to claim 6, wherein said microorganism is a microorganism belonging to the genus Streptomyces.

8. Process according to claim 6, wherein said microorganism is a microorganism belonging to the genus Lactobacillus.

9. Process according to claim 1, wherein said solution containing citric acid or a salt thereof is an aqueous solution having a concentration of more than 0.1 percent expressed as citric acid.

10. Process according to claim 1, wherein said solution containing citric acid or a salt thereof is an aqueous solution having a pH of from 5 to 8.

11. Process according to claim 1, wherein said microbial cell is dipped at least twice in said solution containing citric acid or a salt thereof.

12. Process according to claim 1, wherein said solution containing citric acid or a salt thereof is at a temperature of from 0° to 80° C.

13. Process according to claim 2, wherein drying process is carried out at a temperature of below 50° C.

14. Process according to claim 1, wherein said microbial cell is a microbial cell which has been treated with a flocculant.

15. Process according to claim 1, wherein said microbial cell is treated with a supplemental means following said dipping to improve enzyme retentivity.

16. Process according to claim 15, wherein said microbial cell is subjected to ionizing radiation as a supplemental means.

17. Process according to claim 15, wherein said microbial cell is treated with an aqueous solution of sodium sulfite or cysteine as a supplemental means.

18. Process according to claim 15, wherein said microbial cell is treated with an aqueous solution of glutaraldehyde as a supplemental means.

19. Process according to claim 17, wherein the microbial cell so treated is further dried prior to said contact.

20. Process according to claim 1, wherein the aqueous solution of glucose is so contacted in the presence of magnesium ions.

21. Process according to claim 1, wherein the aqueous solution of glucose is so contacted in the presence of manganese ions.

22. Process according to claim 1, wherein the aqueous solution of glucose is so contacted in the presence of cobalt ions.

* * * * *